United States Patent [19]
Campbell

[11] Patent Number: 5,384,029
[45] Date of Patent: Jan. 24, 1995

[54] ELECTROCHEMICAL MEMBRANE SENSOR

[76] Inventor: Lawrence A. Campbell, 12 Gladstone Av, Hunters Hill, New South Wales 2110, Australia

[21] Appl. No.: 138,403

[22] Filed: Oct. 15, 1993

[51] Int. Cl.[6] .......................................... G01N 27/404
[52] U.S. Cl. ................... 204/415; 204/153.17; 310/311; 310/800
[58] Field of Search .................... 204/153.17, 415

[56] References Cited

U.S. PATENT DOCUMENTS

| | | | |
|---|---|---|---|
| 3,360,451 | 12/1967 | Stack | 204/415 |
| 3,445,364 | 5/1969 | Strickler | 204/405 |
| 3,792,204 | 2/1974 | Murayama et al. | 179/100 |
| 4,170,185 | 10/1979 | Murphy et al. | 114/222 |
| 4,638,207 | 1/1987 | Radice | 310/328 |

FOREIGN PATENT DOCUMENTS

| | | |
|---|---|---|
| 1063016 | 3/1967 | United Kingdom . |
| 1462684 | 1/1977 | United Kingdom . |
| 1491068 | 11/1977 | United Kingdom . |
| 1491886 | 11/1977 | United Kingdom . |
| 2110382 | 6/1983 | United Kingdom . |

*Primary Examiner*—T. Tung
*Attorney, Agent, or Firm*—Abelman, Frayne & Schwab

[57] ABSTRACT

An electrochemical membrane sensor 20 for immersion in a test fluid, such as wastewater, is used to sense desired chemical species, such as dissolved oxygen, within the test fluid. The sensor 20 has an open housing that defines a chamber 24. The chamber 24 is sealed from the test fluid by a membrane 28, so that the chamber 24 can be filled with an electrolytic medium 30. The membrane 28 is selectively permeable so as to allow only the desired chemical species from the test fluid to permeate into the electrolytic medium. Spaced apart within the chamber 24 is a cathode 29 and an anode 29a which are electrically connected to a measurement transducer that responds to current between the cathode 29 and anode 29a. The current is proportional to the concentration of the desired chemical species within the test fluid. The sensor 10 includes means, such as a piezoelectric transducer 22, for agitating the test fluid adjacent the membrane 28 so that the test fluid can be stirred and the outer surface of the membrane can be cleaned prior to sampling by the sensor 10.

8 Claims, 4 Drawing Sheets

ELECTROCHEMICAL MEMBRANE SENSOR

FIELD OF THE INVENTION

The present invention relates to pollution monitoring systems for fluids and, in particular, to electrochemical membrane sensors of water pollution.

BACKGROUND OF THE INVENTION

There is a need to improve the performance and lower the cost of electrochemical membrane sensors, such as dissolved oxygen sensors of the galvanic or polargraphic types, which employ a membrane as an isolation barrier. These sensors are typically used as immersible transducers for the measurement of the quality of test liquid, such as industrial and domestic water and wastewater. They employ a membrane covered electrode system to minimise electrode poisoning or other interferences which would otherwise be experienced by the action of impurities in the test liquid.

In general, the membrane sensors described herein employ a molecular detection system consisting of two solid metal electrodes in contact with a special electrolyte which are separated from the test liquid by a selectively permeable membrane. The basic difference between the galvanic and the polargraphic systems is that, in the former, the electrode reaction is spontaneous (similar to that in a fuel cell), while in the latter, an external source of applied voltage is needed to polarise the indicator electrode.

In the current state of the art, the polargraphic dissolved oxygen sensor (Clark Cell) typically consists of a gold cathode and a silver anode surrounded by a KCl electrolyte. Polyethylene or flourocarbon membranes are commonly used because of their high oxygen permeability and mechanical strength. The Galvanic dissolved oxygen sensor (Mackereth Cell) typically employs gold or silver in the cathode with a lead or cadmium anode. In both types of Cell, the diffusion of oxygen molecules through the membrane causes an electrical current to flow through the Cell which is linearly proportional to the concentration of dissolved oxygen (DO) in the test liquid.

Common DO sensors of this type require stirring or movement of the test liquid to ensure that the test liquid nearest to the membrane does not become depleted of dissolved oxygen and so cause a slower than normal response. When used in dirty liquids, such as heavily laden river water or sewage, these common DO sensors are easily desensitised by deposits of chemical, bacterial and biological contaminants, thus requiring regular membrane replacement.

The present invention overcomes the need for stirring the fluid under test and includes a self cleaning feature to enable more reliable operation in dirty fluids.

BRIEF SUMMARY OF THE INVENTION

According to the invention, there is provided an electrochemical membrane sensor adapted to be immersed in a test fluid so as to sense desired chemical species within the test fluid, said sensor comprising:
an open housing that defines a chamber,
a membrane sealing the chamber from the said test fluid, said chamber adapted to be filled with an electrolytic medium,
said membrane being selectively permeable so as to allow said desired chemical species from the test fluid to permeate into the electrolytic medium,
an anode and a cathode spaced apart within the chamber and each adapted to be electrically connected to a measurement transducer that responds to current between the anode and cathode, said current being proportional to the concentration of said desired chemical species within the test fluid, and
means for agitating the test fluid adjacent the membrane.

Preferably, the agitating means causes the test fluid adjacent the membrane to be stirred so that the concentration of said desired chemical species permeating into the electrolytic medium is representative of the concentration of the desired chemical species in the test fluid as a whole.

It is also preferred that the agitating means causes cleaning of contaminants from the outer surface of the membrane exposed to the test fluid.

The agitating means may comprise an acoustic transduction element. An acoustic transduction element may be incorporated within the sensor so that sonic and ultrasonic energy can be transmitted through the membrane to stir the test fluid adjacent the membrane and clean any contaminants from the outer surface of the membrane.

Preferably, the acoustic transduction element is a piezoelectric transducer. The piezoelectric transducer may be excited to separately produce low frequency vibration modes and high ultrasonic modes.

In a preferred form, the piezoelectric transducer is operated so that in one interval of time it produces low frequency vibration of the membrane so as to stir the test fluid adjacent the membrane, and in another interval of time it transmits high ultrasonic energy through the membrane to clean the outer surface of the membrane.

Preferably, a reading of the measurement transducer is taken during or immediately after operating the piezoelectric transducer in the low frequency vibration mode. Taking a reading after operating the piezoelectric transducer in the high ultrasonic mode may lead to loss of the desired chemical species from the test solution due to cavitation.

Preferably, the test fluid is a liquid such as wastewater and the desired chemical species is dissolved oxygen.

BRIEF DESCRIPTION OF THE DRAWINGS

In order that the invention may be more readily understood and put into practical effect, reference will be made to the accompanying drawings, in which.

DETAILED DESCRIPTION OF THE INVENTION

Figure 1:
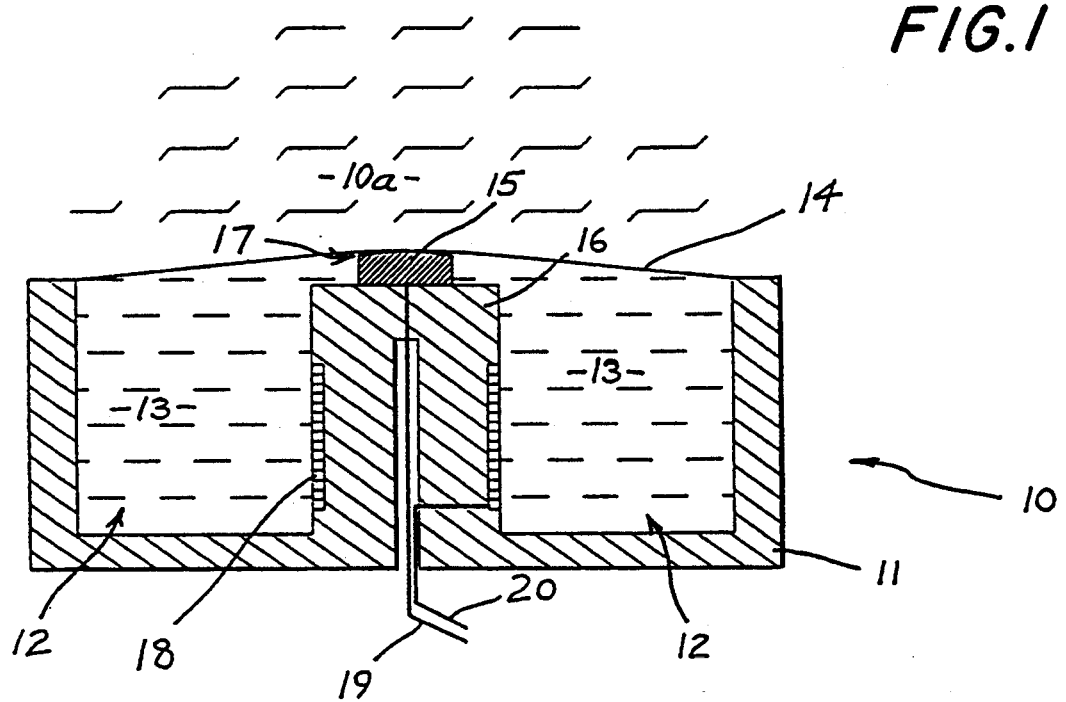
FIG. 1 is a sectional side view of a polargraphic dissolved oxygen sensor or cell common to the prior art.
Figure 2:
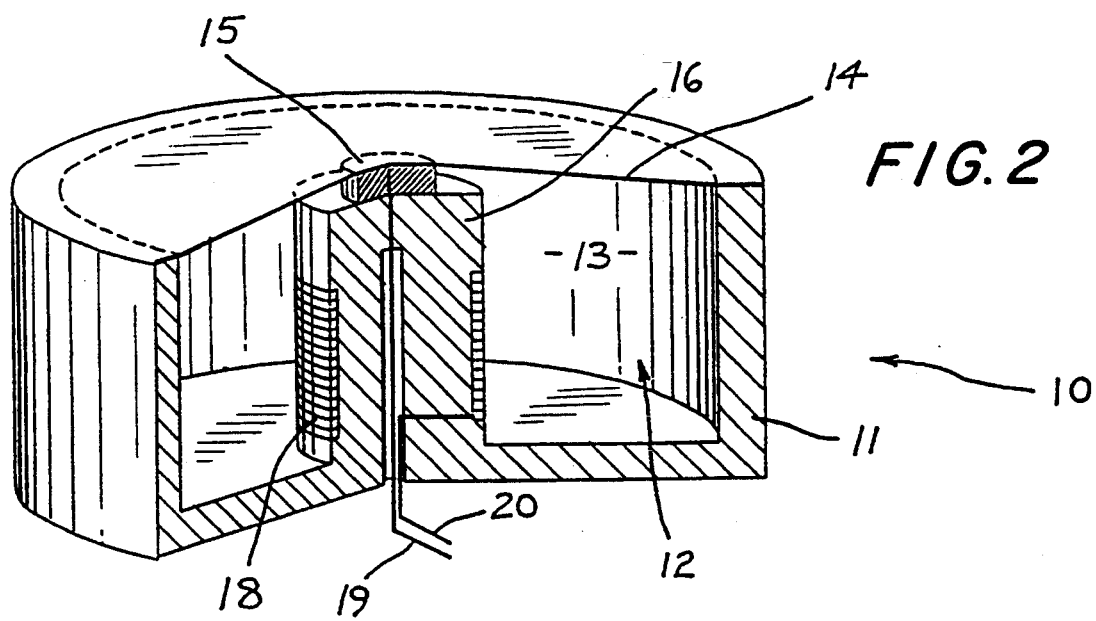
FIG. 2 is a partly broken away perspective view of the sensor of FIG. 1.

Referring to FIGS. 1 and 2, the prior art polargraphic dissolved oxygen (DO) sensor or cell 10, which is immersed in a test liquid 10a, consists of an open housing which, in this instance, is an electrically insulating waterproof and gas impervious plastic housing 11 having a chamber 12 filled with an electrolyte 13 and sealed with a thin membrane 14.

A Gold button cathode 15 is supported by a central column 16, so that it abuts against the membrane 14 with a thin film 17 of electrolyte contained between the cathode 15 and inner surface of the membrane 14.

A silver anode 18 is also in contact with the electrolyte 13. The anode 18 is shown as silver wire wound on the column 16.

Sealed electrical connections 19 and 20 to the cathode 15 and anode 18 respectively provide the output signal of the measurement transducer.

The polorgraphic DO cell 10 operates by diffusion of oxygen molecules from the test liquid 10a through the membrane 14 to the thin film 17 of electrolyte at the cathode 15 where a chemical reaction occurs to release hydroxyl ions into the electrolyte 13. The hydroxyl ions react with the anode 18, oxidising it, and releasing electrons, thereby producing the cell output current that can be sensed by the measurement transducer to give a signal output.

A problem with the accuracy of such a cell is that the test liquid nearest the membrane may become depleted of dissolved oxygen and so cause a slower than normal or erroneous response. Similarly, the outer membrane surface may become contaminated with deposits present in the test liquid and thus require regular membrane replacement.

Figure 3:
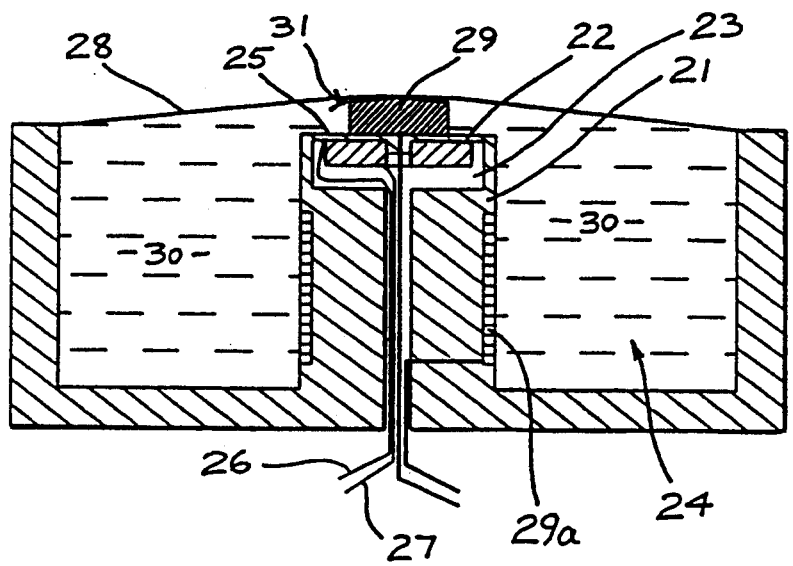
FIG. 3 is a sectional side view of an electrochemical membrane sensor according to a first embodiment of the invention.
Figure 4:
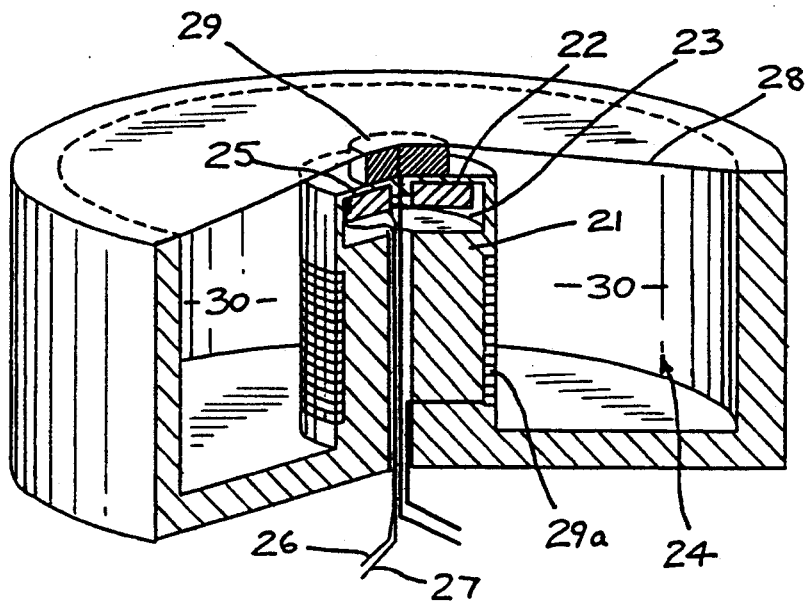
FIG. 4 is a partly broken away perspective view of the sensor of FIG. 3.

The electrochemical membrane sensor 20a shown in FIGS. 3 and 4 embodies certain modifications and improvements over the sensor 10.

Figure 5:
FIG. 5 is a perspective view of an annular piezoelectric crystal incorporated within the sensor of FIGS. 3 and 4.
Figure 6:
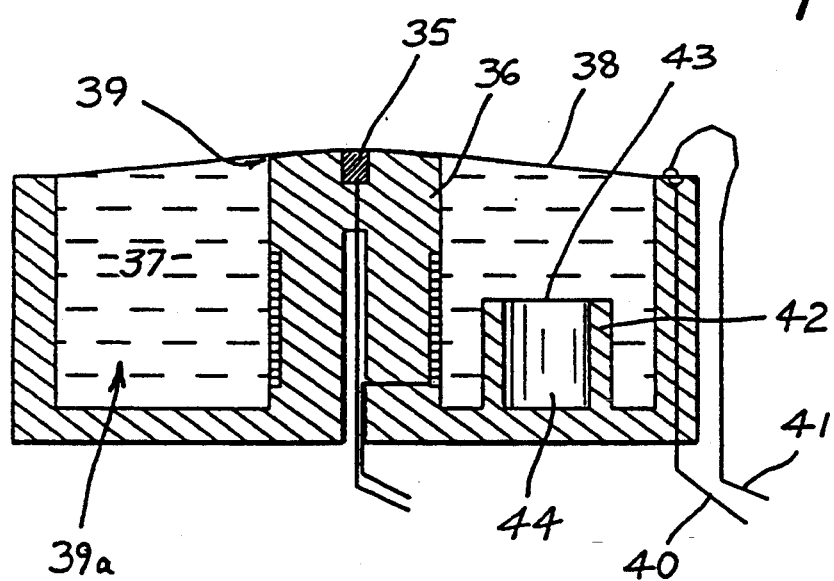
FIG. 6 is a sectional side view of an electrochemical membrane sensor according to a second embodiment of the invention.
Figure 7:
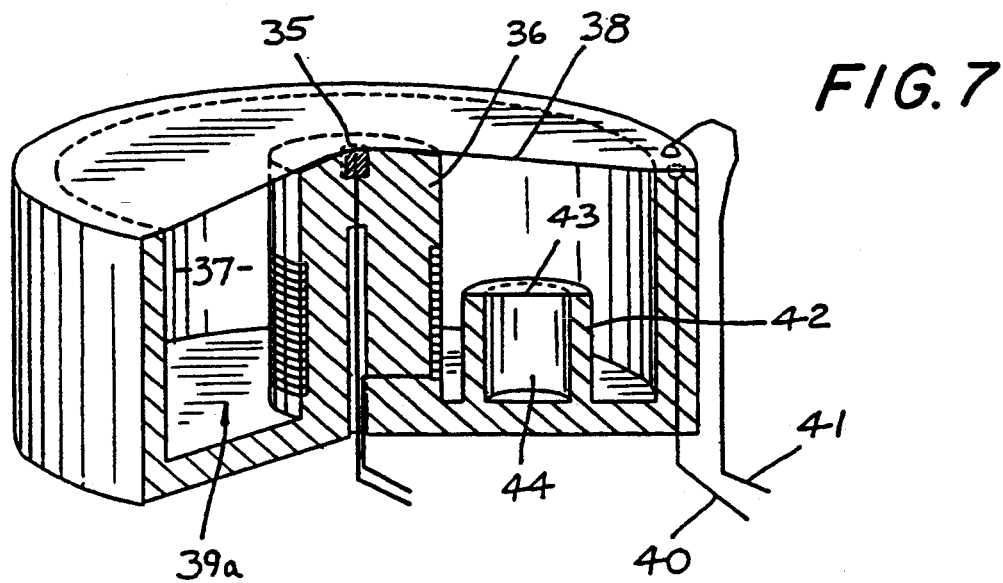
FIG. 7 is a partly broken away perspective view of the sensor of FIG. 6.

The central column 21 is modified to enclose an annular piezoelectric crystal 22 (shown in isolation in FIG. 5) within a cavity 23 which has a gas-tight seal from the electrolyte chamber 24 and contains air, nitrogen or the like. The piezoelectric crystal 22 is attached to the inner face of the thin wall 25 of the cavity 23. The cathode 29 is attached on the outer face of the thin wall 25 and the anode 29a is silver wire, as in the sensor of FIGS. 1 and 2.

The thin wall 25 serves as a flexural diaphragm which resonates in a drum-like mode when the piezoelectric crystal 22 is electrically excited in a thickness vibration mode via the electrical connections, 26 and 27. The resulting mechanical deflection of the thin wall 25 also causes the transmission of acoustic energy through the gold button cathode 29 to the membrane 28 and the adjacent test liquid. The piezoelectric crystal 22 is able to operate in its natural thickness resonance mode to produce ultrasonic energy for cleaning the outer surface of the membrane 28 proximate to the gold button cathode 29. Appropriate low frequency electrical excitation of the piezoelectric crystal 22 causes the complete system to vibrate at its natural mechanical resonance to cause the membrane 28 to induce movement in the test liquid which provides the desired stirring action.

Another advantageous effect of the mechanical excitation of the system is to cause some circulation of fresh electrolyte 30 through the thin electrolyte film 31 to maintain the electrochemical activity of the system.

A further embodiment of the present invention may be achieved by employing piezoelectric film membranes such as polvinylidene fluoride (PVDF), Teflon PFA or the like materials which can be made to exhibit electret and piezoelectric properties while also acting as oxygen permeable membranes. The electret properties are achieved by electrical polarisation and electrically conductive plating across desired areas of the said film membranes to produce capacitive electrodes on opposing sides of the film membranes. In this way, the polarised areas of the film membranes are converted into a piezoelectric transducer to provide the above described cleaning and stirring action.

Oxygen permeable areas of the film membrane may be achieved by leaving those areas of the film membrane in a partially or totally unpolarised state and unplated or partially plated. The partial plating of oxygen permeable areas will act as electrochemical electrodes in the same way as the gold or the like precious metal electrodes employed in conventional Clark or Mackereth cells.

A further extension of the use of electrically polarised film membranes is the ability to utilize their electret polarisation to influence the effective molecular permeability of the sensor membrane and so deliberately enhance or retard the diffusion through the membrane of specific molecules or ions.

FIGS. 6 to 9 illustrate one particular embodiment of the aforementioned piezoelectric film membrane which is oxygen permeable.

The electrode arrangement is very similar to that of FIGS. 1 to 4 with the exception that the gold button cathode 35 is smaller and embedded in the central column 36 so that only a small surface area of the said cathode 35 is exposed to the electrolyte 37. The piezoelectric film membrane 38 seals the chamber 39a with the gold button cathode 35 abutting against the membrane 38 to create a confined thin film of electrolyte 39 between the membrane 38 and the central column 36.

Figure 8:
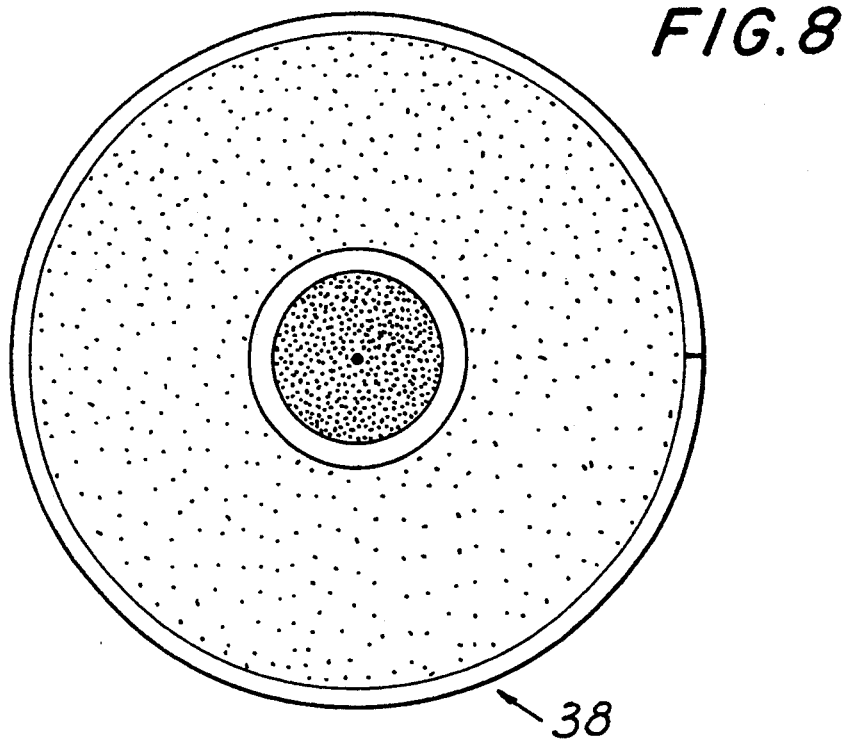
FIG. 8 is a view of the inner surface of the membrane used in the sensor of FIGS. 6 and 7.
Figure 9:
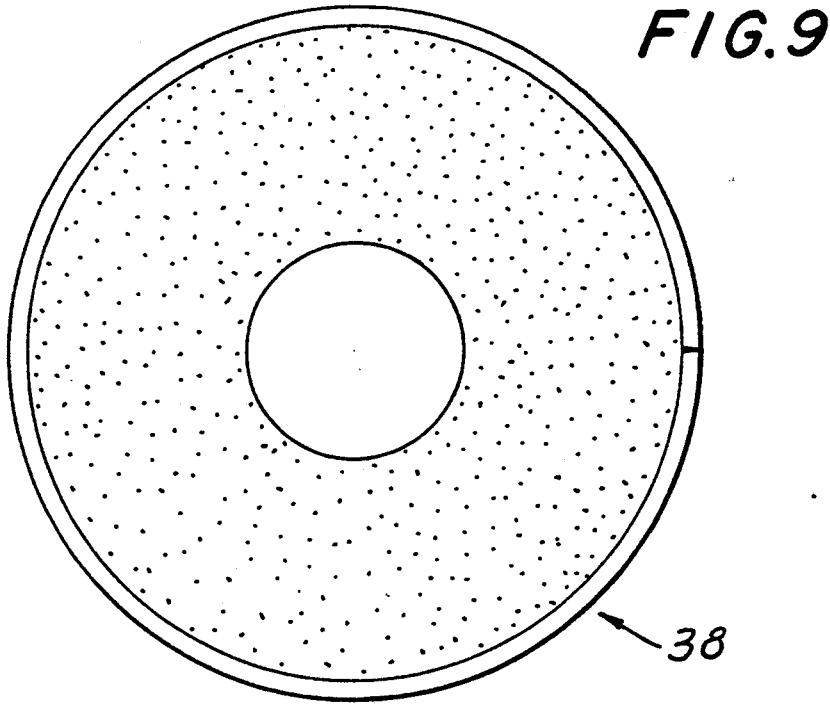
FIG. 9 is a view of the outer surface of the membrane used in the sensor of FIGS. 6 and 7.

FIGS. 8 and 9 illustrate the patterns of gold deposited on the inner and outer surfaces respectively of the said membrane 38, to form the required electrodes and piezoelectric film connections. In FIG. 8, the central dot and grid are designed to make contact with the small gold button cathode 35 to form an extension of the cathode. The outer doughnut rings shown in FIGS. 8 and 9 on both sides of the membrane provide the capacitive plates for exciting the piezoelectric action of membrane 38, whilst electrical connections 40 and 41 provide a circuit for sonic and ultrasonic frequency excitation as described for the embodiment of FIGS. 3 and 4.

During manufacture of such a piezoelectric film membrane, it is poled to hold an electret charge between the two doughnut plates, but can be left unpoled within the centre of the doughnuts plates. In this fashion, the doughnut region has piezoelectric properties, while the central area acts as a normal permeable membrane.

To achieve a suitably low sonic frequency resonance in the system when the piezoelectric film membrane is excited in its stirring mode, mechanical compliance is provided by the internal chamber 42 which is totally gas sealed by a flexible membrane 43 to provide a confined compressible space 44 for a suitable gas such as nitrogen or the like.

One major advantage of the above described construction of a membrane sensor employing metallized film is that it provides a generally applicable means of producing low cost transducers which require precious metal electrodes. In the common Clark cell example of FIGS. 1 and 2, the cost of the solid gold button cathode is often significant and the sensitivity of the cell depends to a large degree upon the surface area of gold which abuts the membrane. The membrane sensor described with respect to FIGS. 6 to 9 allows a large surface area to be achieved with a small amount of gold, and therefore provides a means of producing a low cost, high sensitivity sensor, with or without the above described sonic and ultrasonic stirring and cleaning improvements.

Another advantage in employing metallisation of portions of the membrane surface is that gas permeability can be confined to the unmetallized areas. In DO sensors it is desirable to confine the gas permeable region of the membrane to the area abutting the cathode and block the electrically passive areas to the passage of diffusing molecules. This reduces any unnecessary oxidation of the anode and wastage of the electrolyte reservoir.

Various modifications may be made in details of design and construction without departing from the scope or ambit of the invention.

I claim:

1. An electrochemical membrane sensor adapted to be immersed in a test fluid so as to sense desired chemical species within the test fluid, said sensor comprising:
   an open housing that defines a chamber,
   a membrane sealing the chamber from said test fluid, said chamber adapted to be filled with an electrolytic medium,
   said membrane being selectively permeable so as to allow said desired chemical species from the test fluid to permeate into the electrolytic medium,
   an anode and a cathode spaced apart within the chamber and each adapted to be electrically connected to a measurement transducer that responds to current between the anode and cathode, said current being proportional to the concentration of said desired chemical species within the test fluid, and
   an acoustic transduction element which is adapted to stir the test fluid adjacent the membrane so that the concentration of said desired chemical species permeating into the electrolytic medium is representative of the concentration of the desired chemical species in the test fluid as a whole, and which is also adapted to clean contaminants from the outer surface of the membrane exposed to the test fluid, said acoustic transduction element including said membrane as a mechanical component thereof, wherein said membrane is a piezoelectric film transducer so that sonic and ultrasonic energy transmitted by the piezoelectric action of said membrane will cause the membrane to be excited to separately produce low frequency vibration modes and high frequency ultrasonic modes according to the energy transmitted and to stir the test fluid adjacent the membrane and clean any contaminants from the outer surface of the membrane and to cause circulation of electrolytic medium within the chamber.

2. The electrochemical membrane sensor of claim 1 wherein the test fluid is wastewater and the desired chemical species is dissolved oxygen.

3. The electrochemical membrane sensor of claim 1 wherein the acoustic transduction element includes operation means whereby it may be operated so that in one interval of time it produces low frequency vibration of the membrane so as to stir the test fluid adjacent the membrane, and in another interval of time it transmits high frequency ultrasonic energy through the membrane to clean the outer surface of the membrane.

4. The electrochemical membrane sensor of claim 3, wherein the acoustic transduction element includes a piezoelectric crystal that, when excited to produce low frequency vibration modes, causes vibration of the membrane of the sensor, and, when excited to produce high frequency ultrasonic modes, causes ultrasonic energy to be directed to the membrane of the sensor.

5. The electrochemical membrane sensor of claim 1, wherein said membrane includes a thin film of precious metal selectively deposited on opposing sides of the membrane such that capacitative and electrochemical electrodes are formed thereon.

6. The electrochemical membrane sensor of claim 1 wherein said membrane includes a thin film of gold on the side of the membrane exposed to the electrolytic medium, the thin film of gold serving as the cathode.

7. The electrochemical membrane sensor of claim 6, wherein the thin film of gold forms a grid of permeable and non-permeable regions on said membrane to cover a surface area sufficient to increase sensitivity of the electrochemical membrane sensor.

8. The electrochemical membrane sensor of claim 7, wherein the membrane is made of PVDF.

* * * * *